(12) United States Patent
Haldimann Sanchez et al.

(10) Patent No.: US 9,981,894 B2
(45) Date of Patent: May 29, 2018

(54) INTERMEDIATE COMPOUNDS FOR PRODUCING PERFUMING INGREDIENTS

(71) Applicant: Firmenich SA, Geneva (CH)

(72) Inventors: Murielle Haldimann Sanchez, Geneva (CH); Philippe Dupau, Geneva (CH)

(73) Assignee: Firmenich SA, Geneva (CH)

( * ) Notice: Subject to any disclaimer, the term of this patent is extended or adjusted under 35 U.S.C. 154(b) by 0 days. days.

(21) Appl. No.: 15/542,541

(22) PCT Filed: Jan. 5, 2016

(86) PCT No.: PCT/EP2016/050080
§ 371 (c)(1),
(2) Date: Jul. 10, 2017

(87) PCT Pub. No.: WO2016/113151
PCT Pub. Date: Jul. 21, 2016

(65) Prior Publication Data
US 2018/0002260 A1    Jan. 4, 2018

(30) Foreign Application Priority Data
Jan. 12, 2015 (EP) ..................................... 15150815

(51) Int. Cl.
*C07C 33/34* (2006.01)
*C07C 29/09* (2006.01)
*C07C 69/157* (2006.01)
*C07C 67/297* (2006.01)

(52) U.S. Cl.
CPC ............ *C07C 33/34* (2013.01); *C07C 29/095* (2013.01); *C07C 67/297* (2013.01); *C07C 69/157* (2013.01); *C07C 2602/08* (2017.05)

(58) Field of Classification Search
None
See application file for complete search history.

(56) References Cited

U.S. PATENT DOCUMENTS 6,323,173 B1    11/2001    Winter et al.

FOREIGN PATENT DOCUMENTS

EP    1022265 A1    7/2000

OTHER PUBLICATIONS

Vial ("Synthesis and Optical Resolution of the Floral Odorant (+/−)-2,3-Dihydro-2,5-dimethyl-1H-indene-2-methanol, and Preparation of Analogues" Hevletica Chemica Acta, vol. 88, 2005, p. 3109-3117).*
Fukuoka ("Chemical and Toxicological Studies on Bracken Fern, *Pteridium aquilinum* var. latiusculum. II. Structures of Pterosins, Sesquiterpenes having 1-Indanone Skeleton" Chem. Pharm. Bull., 26(8), 1978, p. 2365-2385).*
International Search Report and Written Opinion, application PCT/EP2016/050080 dated Mar. 21, 2016.
Bhuniya et al., "Enantiomeric scaffolding of tetralone and related scaffolds by EKR and stereoselective ketoreduuction", Org. Biomol. Chem., 2012, vol. 10(3), pp. 536-547.
Bhuniya et al., Org. Biomol. Chem., Supporting Info Part I Contents NMR, 2011, pp. 2-134.
Hasegawa et al., "The first example of samarium diiodide-promoted intramolecular ketone-ester coupling ketones . . . " Tetrahedron Letters, 2006, vol. 47, pp. 7715-7718.
Winter et al., "Synthesis and Odor Properties of Substituted Indane-2-carboxaldehydes." Helvetica Chimica Acta, 2005, vol. 88(12), pp. 3118-3127.
International Preliminary Report on Patentability, Appl. No. PCT/EP2016/050080, dated Jul. 18, 2017.

* cited by examiner

*Primary Examiner* — Jafar Parsa
*Assistant Examiner* — Amy C Bonaparte
(74) *Attorney, Agent, or Firm* — Winston & Strawn LLP

(57) ABSTRACT

The present invention relates to the field of chemical processes and, more particularly, it concerns valuable new chemical intermediates of formula (IV) for producing perfuming ingredients.

15 Claims, No Drawings

INTERMEDIATE COMPOUNDS FOR PRODUCING PERFUMING INGREDIENTS

RELATED APPLICATIONS

This application is a national stage application under 35 U.S.C. § 371 filing of International Patent Application PCT/EP2016/050080, filed Jan. 5, 2016, which claims the benefit of European patent application no 15150815.7 filed Jan. 12, 2015.

TECHNICAL FIELD

The present invention relates to the field of perfumery. More particularly, it concerns valuable new chemical intermediates for producing perfuming ingredients. Moreover, the present invention comprises the also a process for producing said intermediates.

PRIOR ART

EP 1022265 describe a new class of perfuming ingredients, amongst which (2,5-dimethyl-2,3-dihydro-1H-inden-2-yl)methanol is the most know industrially (Lilyflore®, origin: Firmenich SA). Being products of industrial interest, there is always a need for new processes showing an improved yield or productivity.

The compounds (II), which are an object of the present invention, have never been reported or suggested in the context of the preparation of compounds according to EP 1022265. Only a few of said compounds (11) are known have been reported in the prior art, and are (2-methyl-1-oxo-2,3-dihydro-1H-inden-2-yl)methyl acetate, (2-methyl-1-oxo-2,3-dihydro-1H-inden-2-yl)methyl formate and (2-methyl-1H-oxo-2,3-dihydro-1H-inden-2-yl)methyl benzoate reported in Tet. Let. 2006, 7715 in the context of samarium catalysed coupling, as well as (6-methyl-2-methyl-1-oxo-2,3-dihydro-1H-inden-2-yl)methyl acetate in the context of enzymatic kinetic resolutions (see Org. Biomol. Chem, 2012, 10, 536 supplementary material).

Only two compounds (III), which are also an object of the present invention, have been reported in the prior art ((2-methyl-2,3-dihydro-1H-inden-2-yl)methyl acetate and (5-ethyl-2-methyl-2,3-dihydro-1H-inden-2-yl)methyl acetate in Helv. Chim. Acta. 2005, 3118) as precursor of some derivatives of EP 1022265. However, the process reported is very long (at least 4 steps from an indane derivative) and with a poor productivity and require a very different key intermediate ((5-acetyl-2-methyl-2,3-dihydro-1H-inden-2-yl)methyl acetate). This prior art although reporting some derivative of formula (III) cannot be seen as suggesting the present invention.

The aim of the present invention is to provide new solution to the above mentioned need.

DESCRIPTION OF THE INVENTION

We have now surprisingly found that the perfuming ingredients reported in EP 1022265 can be obtained from a new class of precursor (or chemical intermediate), as defined herein below in formula (I), and that said new intermediates allow obtaining the corresponding perfuming ingredients reported in EP 1022265 with overall higher yield and/or productivity, compared to the methods known from the prior art.

In order to overcome the problems aforementioned, the present invention relates to a process for the preparation of a compound of formula

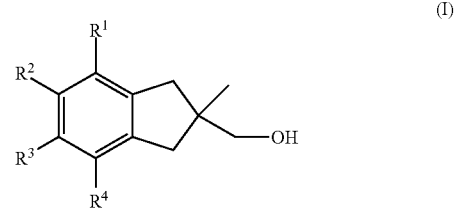

(I)

in the form of any one of its stereoisomers or a mixture thereof, and wherein each $R^1$, $R^2$, $R^3$ and $R^4$, independently from each other, represents a hydrogen atom or a $C_{1-3}$ alkyl group;

characterized in that said process comprises the steps of:

a) reducing a precursor compound of the formula

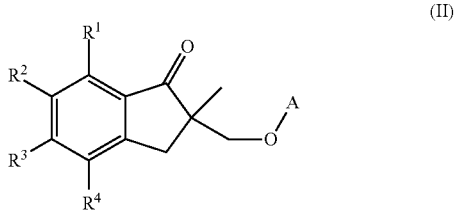

(II)

in the form of any one of its stereoisomers or a mixture thereof, and wherein each $R^1$, $R^2$, $R^3$ and $R^4$, is defined as in formula (I); and A represents a $C_{3-10}$ trialkylsilyl or an RCO group wherein R represents a hydrogen atom, a $C_{1-8}$ alkyl group, or a phenyl optionally substituted by one to three groups selected amongst a $C_{1-3}$ alkyl, alkoxy or amine, groups;

into an indane of formula

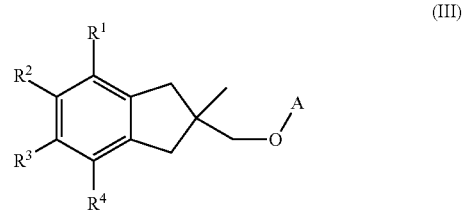

(III)

in the form of any one of its stereoisomers or a mixture thereof, and wherein each $R^1$, $R^2$, $R^3$, $R^4$ and A is defined as in formula (II);

b) hydrolysing the indane of formula (III) into the compound of formula (I).

For the sake of clarity, by the expression "hydrolysing" it is meant any reaction known by a person skilled in the art to convert the ester or silyl ether (III) into the corresponding alcohol (I), regardless of the exact reagent used, e.g. if it is used water, a base, an acid or an alcohol or any other applicable reaction. This type of conversion is very well known by a person skilled in the art and well documented in any handbook of organic chemistry.

For the sake of clarity, steps a) and b) do not need to be performed separately but can also be performed "one pot, i.e. in one after the other but in the reaction medium without previous purification of indane (III). According to any embodiment of the invention, said steps a) and b) are performed separately, i.e. step b) is performed after purification of compound (III).

According to any embodiment of the invention, at least one of said $R^1$, $R^2$, $R^3$ and $R^4$ is a $C_{1-3}$ alkyl group.

According to any embodiment of the invention, two or three of said $R^1$, $R^2$, $R^3$ and $R^4$ represent each a hydrogen atom.

According to a particular embodiment, A represents an acyl group, and the compounds of formula (II) or (III) are of the formulae

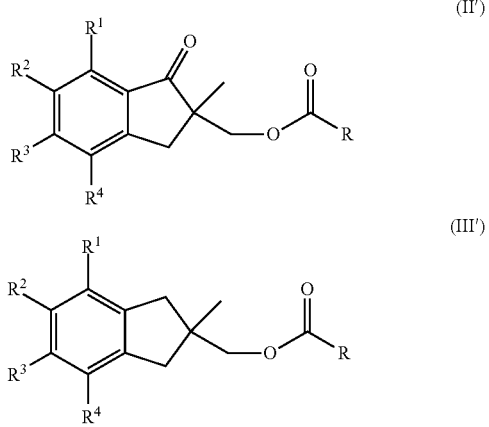

wherein each $R^1$, $R^2$, $R^3$, $R^4$ and R are as defined above.

According to any embodiment of the invention, said R group represents a $C_{1-4}$ alkyl group, or a phenyl optionally substituted by one or two groups selected amongst a $C_{1-3}$ alkyl, alkoxy, groups. Alternatively said R group represents a $C_{1-4}$ alkyl group.

According to any embodiment of the invention, said compounds (I), (II) and (III) are compounds wherein i) $R^1$, $R^2$ and $R^4$ are each a hydrogen atom and $R^3$ is a methyl group, ii) $R^1$, $R^2$ and $R^3$ are each a hydrogen atom and $R^4$ is a methyl group, iii) $R^1$ and $R^4$ are each a hydrogen atom and $R^2$ and $R^3$ are each a methyl group, iv) $R^1$ and $R^3$ are each a hydrogen atom and $R^2$ and $R^4$ are each a methyl group and/or v) $R^1$ and $R^2$ are each a hydrogen atom and $R^3$ and $R^4$ are each a methyl group.

According to any embodiment of the invention, step a) can be advantageously carried out in the presence of a solvent, especially in the case where the compounds (I), (II) and/or (III) are not itself a liquid which could be used as diluent of the medium. It is also well understood by the person skilled in the art that said solvent is a liquid with a melting point below the reaction temperature. In the present invention, the exact nature of the solvent is not a critical element; however, as a person skilled in the art known, the choice of the solvent can be influenced by practical consideration such as the selective solubility of only one of the invention's process products.

Particularly appreciated solvents are $C_{1-9}$ carboxylic acids or corresponding anhydrides and mixture thereof which are liquid at 20° C., such as a $C_{1-4}$ carboxylic acid or, in particular acetic acid.

According to any embodiment of the invention, step a) can be carried out in a broad range of temperature. According to a particular embodiment of the invention, the temperature is comprised between 15° C. and 200° C., more preferably between 40° C. and 160° C. Of course, a person skilled in the art is also able to select the preferred temperature as a function of the melting and boiling point as well as of the specific properties of said solvent as well as of the desired time of reaction or conversion.

According to any embodiment of the invention, the reduction of step a) can be performed by any mean known by a person skilled in the art for a benzylic reduction of a ketone group into the corresponding $CH_2$ group. As non-limiting examples one may cite a catalytic hydrogenation (i.e. using $H_2$ as reducing agent) of the substrate of formula (II) in the presence of a catalyst such as a supported Pd, e.g. supported on charcoal, alumina or silica.

According to any embodiment of the invention, said supported Pd can have a loading (i.e. the w/w ratio Pd/support) comprised between 20% and 1%, or even between 10% and 3%.

According to any embodiment of the invention, the material supporting the Pd can be charcoal, and may have various forms, such as egg-shell, mixed or uniform Pd distribution on charcoal. According to any embodiment of the invention, said supported Pd on charcoal has an egg-shell-type distribution.

The catalyst can be added to the reaction medium in a large range of concentrations. As non-limiting examples, one can cite as complex concentration values those ranging from 0.001 to 10 mol. % relative to the amount of substrate (II). Preferably, the catalyst concentration will be comprised between 0.05-1 mol. %. It goes without saying that the optimum concentration of the catalyst will depend, as the person skilled in the art knows, on the nature of the latter, on the nature and quality of the substrate, on the nature of the solvent used if any, on the reaction temperature and on the pressure of $H_2$ used during the process, as well as the desired time of reaction.

In the hydrogenation process of the invention, the reaction can be carried out at a $H_2$ pressure comprised between 1 and 100 bars or even more if desired. Again, a person skilled in the art is well able to adjust the pressure as a function of the catalyst load and of the dilution of the substrate in the solvent. As examples, one can cite typical pressures of 10 to 50 bars.

Step b) in its own as reported is also an object of the present invention.

As mentioned above, step b) can be carried out in the same reaction medium of step a), at the end of the reduction, or in a separated reaction medium, after purification of compound (II).

According to any embodiment of the invention, if the hydrolysis is carried out as a separate step, then it can be carried out in the presence of a solvent. It is also well understood by the person skilled in the art that said solvent is a liquid with a melting point below the reaction temperature. In the present invention, the exact nature of the solvent is not a critical element; however, as a person skilled in the art known, the choice of the solvent can be influenced by practical consideration such as the selective solubility of only one of the invention's process products. Particularly appreciated solvents are water, $C_{1-3}$ alcohols such as methanol, ethanol, iso-propanol, or mixture thereof.

According to any embodiment of the invention, step b) can be carried out in a broad range of temperature. According to a particular embodiment of the invention, the temperature is comprised between 20° C. and 180° C., more preferably between 40° C. and 14° C. Of course, a person skilled in the art is also able to select the preferred temperature as a function of the melting and boiling point as well as of the specific properties of said solvent as well as the desired time of reaction or conversion.

According to any embodiment of the invention, the hydrolysis of step b) can be performed by any mean known by a person skilled in the art for a hydrolysis of an ester or of a silyl ether. In particular, when A is an acyl, as non-limiting examples on reagent to perform such hydrolysis one may cite water, an alcohol, such as a $C_{1-3}$ alkanol, or a base, such as an alkali hydroxide.

The hydrolysis reagent can be added to the reaction medium in a large range of concentrations. As non-limiting examples, one can cite as hydrolysis concentration values those ranging from 0.8 to 1.2 molar equivalents relative to the amount of substrate (III). Preferably, the catalyst concentration will be comprised between 0.9 to 1.1 molar equivalent. It goes without saying that the optimum concentration of the hydrolysis will depend, as the person skilled in the art knows, on the nature of the latter, on the nature and quality of the substrate, on the nature of the solvent used if any, on the reaction temperature and on the pressure of $H_2$ used during the process, as well as the desired time of reaction.

Typical manners to execute the invention's process are reported herein below in the examples.

The precursors (II) and/or (III) are, generally, novel compounds and present a number of advantages as explained above and shown in the Examples.

Therefore, another object of the present invention concerns the compounds of formula

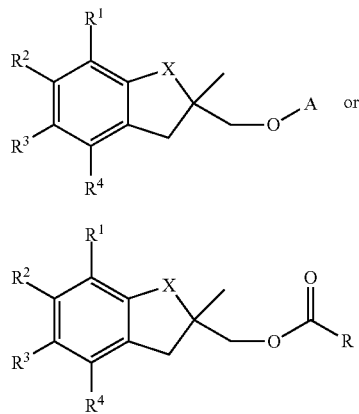

in the form of any one of its stereoisomers or a mixture thereof, and wherein X represents a $CH_2$ or C=O group; and each $R_1$, $R_2$, $R_3$, $R_4$, A and R are as defined in any of the above embodiments for compounds (I), (II), (II'), (III') and (III), provided that (2-methyl-1-oxo-2,3-dihydro-1H-inden-2-yl)methyl acetate, (2-methyl-1-oxo-2, 3-dihydro-1H-inden-2-yl)methyl formate, (2-methyl-1-oxo-2,3-dihydro-1H-inden-2-yl)methyl benzoate, ((2-methyl-2,3-dihydro-1H-inden-2-yl)methyl acetate, (6-methyl-2-methyl-1-oxo-2,3-dihydro-1H-inden-2-yl) acetate and (5-ethyl-2-methyl-2,3-dihydro-1H-inden-2-yl)methyl acetate are excluded.

According to a particular embodiment of the compound (IV), said compound is a compound of formula (II).

Said compound (IV), when X is a carbonyl group, can be obtained by reacting the desired methyl indanone (V)

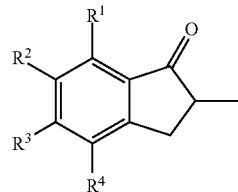

wherein $R^1$, $R^2$, $R^3$ and $R^4$ are as defined in any of the above embodiments with formaldehyde and a suitable carboxylic anhydride of formula RCOOOCR.

This reaction is generally known by a person skilled in the art (aldol and esterification reactions) and one particular embodiment is exemplified in the Examples.

The process for the preparation of compound (II) can be carried out in a broad range of temperature. According to a particular embodiment of the invention, the temperature is comprised between 10° C. and 100° C., more preferably between 20° C. and 70° C. Of course, a person skilled in the art is also able to select the preferred temperature as a function of the melting and boiling point, as well as of the specific properties of said solvent, and of the desired time of reaction or conversion.

Typical manners to execute the invention's process are reported herein below in the examples.

EXAMPLES

The invention will now be described in further detail by way of the following examples, wherein the temperatures are indicated in degrees centigrade and the abbreviations have the usual meaning in the art.

All reagents and solvents were used as purchased in technical grade without further purification. NMR spectra were recorded on a Bruker AM-400 ($^1$H at 500.1 M, $^{13}$C at 125.7 MHz) spectrometer and normally measured at 300 K, in $CDCl_3$ unless indicated otherwise. Chemical shifts are listed in ppm, and coupling constant in Hz. IR spectra were recorded on a Perkin Elmer FT-IR spectrometer, and the frequencies are given in $cm^{-1}$.

Example 1

Preparation of (2,5-dimethyl-2,3-dihydro-1H-inden-2-ylmethanol

A) According to the Invention

Preparation of (2,5-dimethyl-J-oxo-2,3-dihydro-1H-inden-2-yl)methyl acetate 2,5-dimethyl-2,3-dihydro-1H-inden-1-one, methanol (1 Eq.)) and $K_2CO_3$ (0.85 mol. %) were loaded altogether in a three-necked round-bottomed flask and heated to 60° C. Formaldehyde (1.03 mol. eq., 55 wt. % solution in water/methanol mixture) was then introduced in 1 hour. 30 Minutes after addition completion (complete reaction conversion was checked by GC analysis), acetic acid (1.7 mol. %) was added to quench potassium carbonate and methanol was completely removed under reduced pressure. Obtained crude 2-(hydroxymethyl)-2,5-dimethyl-2,3-dihydro-1H-inden-1-one was then heated to 100° C. and acetic anhydride (1.4 mol. eq.) was introduced in 2 hours. Reaction mixture was left stirring at this temperature for an additional 4 hours. (2,5-dimethyl-1-oxo-2,3-dihydro-1H-inden-2-yl)methyl acetate, acetic acid formed during the reaction and excess acetic anhydride were flash distilled altogether.

After complete removal of lights, 2,5-dimethyl-1-oxo-2,3-dihydro-1H-inden-2-yl)methyl acetate was determined to be obtained with more than 99 mol. % yield as a solid.

$^1$H NMR: 1.22 (s, 3H, CH3), 1.92 (s, 3H, CH3), 2.45 (s, 3H, CH3), 2.87 (d, J=17.0, 1H, CH2), 3.22 (d, J=17.0, 1H, CH2), 4.20 (dd, J=17.2 and 10.8, 2H, CH2), 7.20 (d, J=8.0, 1H), 7.26 (s, 1H), 7.66 (d, J=8.0, 1H).

$^{13}$C NMR: 20.69 (CH3), 21.17 (CH3), 22.12 (CH3), 37.87 (CH2), 48.96 (C), 68.31 (CH2), 124.22 (CH), 126.95 (CH), 128.86 (CH), 133.30 (C), 146.40 (C), 152.95 (C), 170.83 (CO ester), 207.40 (CO ketone).

Preparation of
(2,5-dimethyl-2,3-dihydro-1H-inden-2-yl)methyl
acetate

Flash distilled (2,5-dimethyl-1-oxo-2,3-dihydro-1H-inden-2-yl)methyl acetate (containing about 1 mol. eq. acetic acid and 0.4 mol. eq. acetic anhydride), acetic acid (1 mol. eq.) and Pd/C (0.15 mol. % Pd relative to the stating keto acetate, egg-shell type—Escat® 167) were loaded altogether in an autoclave. After purging with nitrogen (3 times 5 bars) and hydrogen (3 times 5 bars), the autoclave was pressurized to 30 bars hydrogen and progressively heated to 140° C. while maintaining hydrogen pressure constant during the whole reaction. After an overall 6 hours, the autoclave was cooled down to room temperature, depressurized and purged with nitrogen. Heterogeneous catalyst was then filtered off and remaining organic phase was concentrated under vacuum for lights removal.

After flash distillation, desired 2,5-dimethyl-2,3-dihydro-1H-inden-2-yl)methyl acetate was determined to be obtained in 98 mol. % yield as oil.

$^1$H NMR: 1.16 (s, 3H, CH3), 2.05 (s, 3H, CH3), 2.30 (s, 3H, CH3), 2.63 (d, J=15.6, 2H, CH2), 2.87 (d, J=5.8, 1H, CH2), 2.90 (d, J=5.8, 1H, CH2), 3.99 (s, 2H, CH2), 6.94 (d, J=7.8, 1H), 6.98 (s, 1H), 7.04 (d, J=7.8, 1H).

$^{13}$C NMR: 20.89 (CH3), 21.23 (CH3), 24.31 (CH3), 42.69 (CH2), 42.99 (CH2), 43.31 (C), 71.30 (CH2), 124.52 (CH), 125.51 (CH), 127.13 (CH), 135.91 (C), 138.98 (C), 142.20 (C), 171.26 (CO ester).

Preparation of
(2,5-dimethyl-2,3-dihydro-1H-inden-2-yl)methanol

Concentrated crude 2,5-dimethyl-2,3-dihydro-1H-inden-2-yl)methyl acetate, ethanol (1 wt. eq.) and water (0.5 wt. eq.) were loaded together into a three-necked round-bottomed flash and the mixture was heated to 60° C. KOH (1.05 eq. 45% aqueous solution) was introduced in 2 hours. Upon addition completion, ethanol was removed under slight vacuum. After cooling down to room temperature, heptanes (1.5 wt. eq.) was added and the lower aqueous phase was discarded. The upper organic phase was washed twice with water and heptane concentration allowed azeotropic removal of water. Crude product was then flash distilled to afford desired (2,5-dimethyl-2,3-dihydro-1H-inden-2-yl) methanol in 98% yield (i.e. quantitative yield for the saponification reaction).

B) According to the Prior Art (EP 1022265)

Preparation of 2-(hydroxymethyl)-2,5-dimethyl-2,3-dihydro-1H-inden-1-one and its Direct Hydrogenation into (2,5-dimethyl-2,3-dihydro-1H-inden-2-yl) methanol 2,5-dimethyl-2,3-dihydro-1H-inden-1-one, methanol (1 wt. Eq.)) and K$_2$CO$_3$ (0.85 mol. %) were loaded altogether in a three-necked round-bottomed flask and heated to 60° C. Formaldehyde (1.03 mol. eq., 55 wt. % solution in water/methanol mixture) was then introduced in 1 hour. 30 Minutes after addition completion (complete reaction conversion was checked by GC analysis), acetic acid (1.7 mol. %) was added to quench potassium carbonate and methanol was completely removed under reduced pressure. Obtained crude 2-(hydroxymethyl)-2,5-dimethyl-2,3-dihydro-1H-inden-1-one was flash distilled under high vacuum.

$^1$H NMR: 1.20 (s, 3H, CH3), 2.42 (s, 3H, CH3), 2.75 (broad t, J=5.5, 1H, OH), 2.82 (d, J=17.2, 1H, CH2), 3.21 (d, J=5.8, 1H, CH2), 3.59 (dd, J=10.8 and 4.1, 1H, CH2), 3.80 (dd, J=10.8 and 6.2, 1H, CH2), 7.14 (d, J=8.2, 1H), 7.25 (s, 1H), 7.59 (d, J=8.2, 1H).

$^{13}$C NMR: 20.70 (CH3), 22.10 (CH3), 37.79 (CH2), 51.04 (C), 67.81 (CH2), 124.02 (CH), 126.99 (CH), 128.74 (CH), 133.52 (C), 146.23 (C), 153.88 (C), 210.67 (CO ketone).

Hydrogenation of 2-(hydroxymethyl)-2,5-dimethyl-2,3-dihydro-1H-inden-1-one under the above reported conditions afforded (2,5-dimethyl-2,3-dihydro-1H-inden-2-yl) methanol with incomplete conversion even after 24 hours and about 65% yield based on product GC purity after lights removal and flash distillation to remove heavy by-products.

As a conclusion, starting from 2,5-dimethyl-2,3-dihydro-1H-inden-1-one, going through the acetate derivative allowed to obtain (2,5-dimethyl-2,3-dihydro-1H-inden-2-yl) methanol with an overall 97-98% molar yield compared to about 64% for the direct route.

Example 2

Influence of Nature of Carboxylic Acid as a Solvent on (2,5-dimethyl-1-oxo-2,3-dihydro-1H-inden-2-yl)methyl acetate Hydrogenation/Hydrogenolysis Reaction Neat distilled (2,5-dimethyl-1-oxo-2,3-dihydro-1H-inden-2-yl)methyl acetate, carboxylic acid (2 mol. eq.), acetic anhydride (0.4 mol. eq.) and Pd/C (0.15 mol. % Pd) were loaded altogether in an autoclave. After purging with nitrogen (3 times 5 bars) and hydrogen (3 times 5 bars), the autoclave was pressurized to 30 bars hydrogen and progressively heated to 140° C. while maintaining hydrogen pressure constant during the whole reaction. After complete conversion (checked by GC analysis) or 24 h in case of partial conversion, the autoclave was cooled down to room temperature, depressurized and purged with nitrogen. Heterogeneous catalyst was then filtered off and remaining organic phase was concentrated under vacuum for lights removal. Desired product was generally obtained as a mixture of free alcohol (minor), acetate and ester derived from carboxylic acid used as a solvent. Reaction yields were determined after bulb to bulb distillation in order to determine the quantity of residues eventually formed during de reaction and quantitative saponification reaction to afford (2,5-dimethyl-2,3-dihydro-1H-inden-2-yl)methanol as the sole product.

| Solvent (RCO$_2$H) | Time to completion (h) | Selectivity (GC %) | Alcohol/acetate/ester GC % ratio [a] | Yield [b] (mol. %) |
|---|---|---|---|---|
| CH$_3$CO$_2$H | 6 h | 99% | 1/99 | 98% |
| C$_2$H$_5$CO$_2$H | 8 h | 98% | 3/59/38 | 96% |
| C$_3$H$_7$CO$_2$H | 10 h | 97% | 4/52/44 | 94% |
| (CH$_3$)$_2$CHCO$_2$H | 10 h | 97% | 5/80/15 | 95% |

[a] alcohol/acetate/ester ratio is depending on reaction duration
[b] final yield in (2,5-dimethyl-2,3-dihydro-1H-inden-2-yl)methanol Example 3

Influence of Nature of the Ester Moiety on (2,5-dimethyl-1-oxo-2,3-dihydro-1H-inden-2-yl)methyl carboxylate Hydrogenation/Hydrogenolysis Reaction 3.1) Synthesis of 2,5-dimethyl-1-oxo-2,3-dihydro-1H-inden-2-yl)methyl carboxylates General procedure: 2,5-dimethyl-2,3-dihydro-1H-inden-1-one, methanol (1 wt. eq.)) and K$_2$CO$_3$ (0.85 mol. %) were loaded altogether in a three-necked round-bottomed flask and heated to 60° C. Formaldehyde (1.03 mol. eq., 55 wt. % solution in water/methanol mixture) was then introduced in 1 h in order to easily control reaction exothermy. 30 minutes after addition completion (complete reaction conversion was checked by GC analysis), carboxylic acid RCO$_2$H (1.7 mol. %) was added to quench potassium carbonate and methanol was completely removed under reduced pressure. Obtained crude 2-(hydroxymethyl)-2,5-dimethyl-2,3-dihydro-1H-inden-1-one was then heated to 100° C. and carboylic anhydride (RCO)$_2$O (1.4 mol. eq.) was introduced in 2 h. Reaction mixture was left stirring at this temperature for some additional 4 hours (complete reaction conversion was checked by GC analysis). After removal of lights (excess carboxylic anhydride and corresponding carboxylic acid formed) (2,5-dimethyl-1-oxo-2,3-dihydro-1H-inden-2-yl)methyl carboxylate, was purified by distillation under vacuum.

(2,5-dimethyl-1-oxo-2,3-dihydro-1H-inden-2-yl)methyl acetate was thus obtained as a white solid with more than 99 mol. % yield and was characterized by NMR analysis.
$^1$H-NMR: 1.22 (s, 3H, CH$_3$), 1.92 (s, 3H, CH$_3$), 2.45 (s, 3H, CH$_3$), 2.87 (4, J=17.0, 1 H, CH$_2$), 3.22 (d, J=17.0, 1 H, CH$_2$), 4.19 (d, J=10.8, 1H, CH$_2$), 4.22 (d, J=10.8, 1H, CH$_2$), 7.20 (d, J=8.0, 1H, CH), 726 (s, 1H, CH), 7.66 (d, J=8.0§, 1H, CH).
$^{13}$C-NMR: 20.69 (CH$_3$), 21.17 (CH$_3$), 22.12 (CH$_3$), 37.87 (CH$_2$), 48.96 (C), 68.31 (CH$_2$), 124.22 (CH), 126.95 (CH), 128.86 (CH), 133.30 (C), 146.40 (C), 152.95 (C), 170.83 (CO ester), 207.40 (CO ketone).

(2,5-dimethyl-1-oxo-2,3-dihydro-1H-inden-2-yl)methyl propionate was thus obtained as a colorless viscous liquid with 80 mol. % yield in 97.5% GC purity and was characterized by NMR analysis.
$^1$H-NMR: 0.98 (t, J=7.6, 3H, CH$_3$), 1.22 (s, 3H, CH$_3$), 2.18 (q, J=7.6, 2H, CH$_2$), 2.45 (s, 3H, CH$_3$), 2.87 (d, J=17.2, 1H, CH$_2$), 3.21 (d, J=17.2, 1 H, CH$_2$), 4.20 (d, J=10.8, 1H, CH$_2$), 4.22 (d, J=10.8, 1H, CH$_2$), 7.19 (d, J=7.8, 1H, CH), 7.26 (s, 1H, CH), 7.65 (d, J=7.8, 1H, CH).
$^{13}$C-NMR: 8.93 (CH$_3$), 21.06 (CH$_3$), 22.11 (CH$_3$), 27.37 (CH$_2$), 37.97 (CH$_2$), 49.05 (C), 68.24 (CH$_2$), 124.17 (CH), 126.90 (CH), 128.84 (CH), 133.40 (C), 146.37 (C), 152.99 (C), 174.15 (CO ester), 207.47 (CO ketone).

(2,5-dimethyl-1-oxo-2,3-dihydro-1H-inden-2-yl)methyl butyrate was thus obtained as a colorless viscous liquid with 85 mol. % yield in 97.7% GC purity and was characterized by NMR analysis.
$^1$H-NMR: 0.83 (t, J=7.4, 3H, CH$_3$), 1.22 (s, 3H, CH$_3$), 1.48 (sext, J=7.4, 2H, CH$_2$), 2.14 (t, J=7.4, 2H, CH$_2$), 2.45 (s, 3H, CH$_3$), 2.87 (d, J=17.1, 1H, CH$_2$), 3.21 (d, J=17.1, 1H, CH$_2$), 4.19 (d, J=10.8, 1H, CH$_2$), 4.22 (d, J=10.8, 1 H, CH$_2$), 7.19 (d, J=8.0, 1H, CH), 7.26 (s, 1H, CH), 7.65 (d, J=8.0, 1H, CH).
$^{13}$C-NMR: 15.53 (CH$_3$), 18.24 (CH$_2$), 21.06 (CH$_3$), 22.11 (CH$_3$), 35.95 (CH$_2$), 37.98 (CH$_2$), 49.03 (C), 68.19 (CH$_2$), 124.17 (CH), 126.90 (CH), 128.83 (CH), 133.41 (C), 146.35 (C), 152.99 (C), 173.35 (CO ester), 207.47 (CO ketone).

(2,5-dimethyl-1-oxo-2,3-dihydro-1H-inden-2-yl)methyl isobutyrate was thus obtained as a colorless viscous liquid with 95 mol. % yield in 96.8% GC purity and was characterized by NMR analysis.
$^1$H-NMR: 0.97 (d, J=6.8, 3H, CH), 0.99 (d, J=6.8, 3H, CH), 1.23 (s, 3H, CH$_3$), 2.38 (hept, J=6.8, 1 H, CH), 2.44 (s, 3H, CH$_3$), 2.87 (d, J=17.0, 1H, CH$_2$), 3.20 (d, J=17.0, 1H, CH$_2$), 4.20 (s, 2H, CH$_2$), 7.19 (d, J=8.0, 1H, CH), 7.25 (s, 1H, CH), 7.66 (d, J=8.0, 1 H, CH).
$^{13}$C-NMR: 18.68 (CH$_3$), 18.77 (CH$_3$), 20.91 (CH$_3$), 22.11 (CH$_3$), 33.85 (CH), 38.00 (CH$_2$), 49.13 (C), 68.26 (CH$_2$), 124.12 (CH), 126.82 (CH), 128.82 (CH), 133.49 (C), 146.35 (C), 153.03 (C), 176.67 (CO ester), 207.50 (CO ketone).

(2,5-dimethyl-1-oxo-2,3-dihydro-1H-inden-2-yl)methyl pivalate was thus obtained as a colorless viscous liquid with 79 mol. % yield in 96.6% GC purity and was characterized by NMR analysis.
$^1$H-NMR: 0.98 (s, 9H, 3 CH$_3$), 1.23 (s, 3H, CH$_3$), 2.44 (s, 3H, CH$_3$), 2.89 (d, J=17.0, 1H, CH$_2$), 3.19 (d, J=17.0, 1H, CH$_2$), 4.18 (s, 2H, CH$_2$), 7.19 (d, J=8.0, 1H, CH), 7.25 (s, 1H, CH), 7.65 (d, J=8.0, 1H, CH).
$^{13}$C-NMR: 20.68 (CH$_3$), 22.10 (CH$_3$), 26.89 (3 CH$_3$), 38.12 (CH$_2$), 38.70 (C), 49.13 (C), 68.58 (CH$_2$), 124.03 (CH), 126.74 (CH), 128.80 (CH), 133.60 (C), 146.31 (C), 153.06 (C), 177.98 (CO ester), 207.52 (CO ketone).

(2,5-dimethyl-1-oxo-2,3-dihydro-1H-inden-2-yl)methyl hexanoate was thus obtained as a colorless viscous liquid with 95 mol. % yield in 98.2% GC purity and was characterized by NMR analysis.
$^1$H-NMR: 0.83 (t, J=7.0, 3H, CH$_3$), 1.12-1.21 (m, 4H, 2 CH$_2$), 1.22 (s, 3H, CH), 1.43 (quint, J=7.6, 2H, CH$_2$), 2.15 (t, J=7.6, 2H, CH$_2$), 2.45 (s, 3H, CH$_3$), 2.87 (d, J=17.0, 1H, CH$_2$), 3.21 (d, J=17.0, 1H, CH$_2$), 4.21 (s, 2H, CH$_2$), 7.19 (d, J=8.0, 1H, CH), 7.25 (s, 1H, CH), 7.66 (d, J=8.0, 1 H, CH).
$^{13}$C-NMR: 13.82 (CH$_3$), 21.03 (CH$_3$), 22.11 (CH$_3$), 22.23 (CH$_2$), 24.45 (CH$_2$), 31.16 (CH$_2$), 34.08 (CH$_2$), 37.99 (CH$_2$), 49.02 (C), 68.23 (CH$_2$), 124.17 (CH), 126.88 (CH), 128.83 (CH), 133.45 (C), 146.34 (C), 153.01 (C), 173.51 (CO ester), 207.48 (CO ketone).

(2,5-dimethyl-1-oxo-2,3-dihydro-1H-inden-2-yl)methyl benzoate was synthesized according to some slightly different procedure due to the physical aspect of benzoic anhydride, benzoic acid formed during the reaction and desired product. To a solution of crude 2-(hydroxymethyl)-2,5-dimethyl-2,3-dihydro-1H-inden-1-one obtained as an intermediate according to general procedure in toluene was added at 100° C. in 2 h molten benzoic anhydride (1.4 eq.). Reaction mixture was then left stirring at reflux for some additional 4 hours (complete reaction conversion was checked by GC analysis). After cooling to 50° C., pH was brought up to 10 by slow addition of 20 wt. % aqueous $KHCO_3$ for benzoic acid removal. After decantation of the aqueous phase, the organic mixture was washed with water and toluene was then removed under vacuum. Treatment with butanol under reflux then allowed to quench excess benzoic anhydride. After butanol removal, distillation under vacuum afforded desired (2,5-dimethyl-1-oxo-2,3-dihydro-1H-inden-2-yl)methyl benzoate as a white solid with 75 mol. % yield in 97.6% GC purity. (2,5-dimethyl-1-oxo-2,3-dihydro-1H-inden-2-yl)methyl benzoate was characterized by NMR analysis.

$^1$H-NMR: 1.32 (s, 3H, $CH_3$), 2.45 (s, 3H, $CH_3$), 2.95 (d, J=17.2, 1H, $CH_2$), 3.30 (d, J=17.2, 1H, $CH_2$), 4.43 (s, 2H, $CH_2$), 7.22 (d, J=7.8, 1H, CH), 7.26 (s, 1H, CH), 7.28-7.32 (m, 2H, 2 CH), 7.47 (tt, J=7.5 and 1.3, 1H, CH), 7.69-7.74 (m, 3H, 3 CH).

$^{13}$C-NMR: 20.85 ($CH_3$), 22.12 ($CH_3$), 38.22 ($CH_2$), 49.25 (C), 69.15 ($CH_2$), 124.23 (CH), 126.92 (CH), 128.24 (2 CH), 128.86 (CH), 129.48 (2 CH), 129.77 (C), 132.94 (CH), 133.51 (C), 146.42 (C), 153.03 (C), 166.14 (CO ester), 207.41 (CO ketone).

$^{13}$C-NMR: 21.13 ($CH_3$), 22.12 ($CH_3$), 37.83 ($CH_2$), 48.73 (C), 67.77 ($CH_2$), 124.27 (CH), 126.99 (CH), 128.98 (CH), 133.18 (C), 146.61 (C), 152.85 (C), 160.64 (OCOH ester), 207.07 (CO ketone).

3.2) (2,5-dimethyl-1-oxo-2,3-dihydro-1H-inden-2-yl)methyl carboxylate Hydrogenation/Hydrogenolysis Reaction Neat distilled (2,5-dimethyl-1-oxo-2,3-dihydro-1H-inden-2-yl)methyl carboxylate, acetic acid (2 mol. eq.), acetic anhydride (0.4 mol. eq.) and Pd/C (0.15 mol. % Pd) were loaded altogether in an autoclave. After purging with nitrogen (3 times 5 bars) and hydrogen (3 times 5 bars), the autoclave was pressurized to 30 bars hydrogen and progressively heated to 140° C. while maintaining hydrogen pressure constant during the whole reaction. After complete conversion (checked by GC analysis) or 24 h in case of partial conversion, the autoclave was cooled down to room temperature, depressurized and purged with nitrogen. Heterogeneous catalyst was then filtered off and remaining organic phase was concentrated under vacuum for lights removal. Desired product was generally obtained as a mixture of free alcohol (minor), acetate and initial ester derivative. Reaction yields were determined after bulb to bulb distillation in order to determine the quantity of residues eventually formed during de reaction and quantitative saponification reaction to afford (2,5-dimethyl-2,3-dihydro-1H-inden-2-yl)methanol as the sole product.

| Ester substrate | Time to completion (h) | Selectivity (GC %) | Alcohol/acetate/ester GC % ratio [a] | Yield [b] (mol. %) |
|---|---|---|---|---|
| $OCOCH_3$ | 6 h | 99% | 1/99 | 98% |
| $OCOC_2H_5$ | 6 h | 99% | 1/46/54 | 98% |
| $OCOC_3H_7$ | 10 h | 97% | 1/35/64 | 96% |
| $OCOCH(CH_3)_2$ | 10 h | 98% | 1/29/70 | 97% |
| $OCOC(CH_3)_3$ | 16 h | 96% | 1/4/95 | 95% |
| $OCOC_5H_{11}$ | 12 h | 96% | 1/32/67 | 95% |
| OCOH | 12 h | 92% | 1/70/29 | 90% |
| OCOPh | 18 h | 98% | 1/4/95 | 97% |

[a] alcohol/acetate/ester ratio is depending on reaction duration
[b] final yield in (2,5-dimethyl-2,3-dihydro-1H-inden-2-yl)methanol (2,5-dimethyl-1-oxo-2,3-dihydro-1H-inden-2-yl)methyl formate was synthesized according to some different procedure. After heating a 2.83 eq./2.5 eq. acetic anhydride/formic acid mixture at 50° C. for 1 h crude 2-(hydroxymethyl)-2,5-dimethyl-2,3-dihydro-1H-inden-1-one obtained as an intermediate according to general procedure was added at 0° C. in 1 h and the reaction mixture was left stirring at 25° C. for additional 4 h (complete conversion detected by GC analysis). After removal of the lights under vacuum, toluene was added to crude product and the organic mixture was washed with water, 10 wt. % aqueous $KHCO_3$ and water. After toluene removal, distillation under vacuum afforded desired (2,5-dimethyl-1-oxo-2,3-dihydro-1H-inden-2-yl)methyl formate as a colorless liquid with 95 mol. % yield in 98.2% GC purity. (2,5-dimethyl-1-oxo-2,3-dihydro-1H-inden-2-yl)methyl formate was characterized by NMR analysis.

$^1$H-NMR: 1.24 (s, 3H, $CH_3$), 2.45 (s, 3H, $CH_3$), 2.90 (d, J=17.2, 1H, $CH_2$), 3.24 (d, J=17.2, 1H, $CH_2$), 4.27 (d, J=10.8 and 0.6, 1H, $CH_2$), 4.33 (dd, J=10.8 and 0.6, 1H, $CH_2$), 7.21 (d, J=7.8, 1H, CH), 7.27 (s, 1H, CH), 7.66 (d, J=7.8, 1H, CH), 7.94 (s, 1H, OCOH).

(2,5-dimethyl-2,3-dihydro-1H-inden-2-yl)methyl formate $^1$H-NMR: 1.18 (s, 3H, $CH_3$), 2.30 (s, 3H, $CH_3$), 2.66 (broad d, J=15.6, 2H, 2 $CH_2$), 2.89 (dd, J=15.6 and 5.4, 2H, 2 CH), 4.08 (d, J=0.8, 2H, $CH_2$), 6.95 (d, J=7.6, 1H, CH), 6.99 (s, 1H, CH), 7.05 (d, J=7.6, 1H, CH), 8.09 (broad s, 1H, OCOH).

$^{13}$C-NMR: 21.23 ($CH_3$), 24.28 ($CH_3$), 42.67 ($CH_2$), 42.98 ($CH_2$), 43.19 (C), 70.76 ($CH_2$), 124.55 (CH), 125.53 (CH), 127.23 (CH), 136.02 (C), 138.75 (C), 141.97 (C), 161.18 (OCOH ester).

((2,5-dimethyl-2,3-dihydro-1H-inden-2-yl)methyl acetate $^1$H-NMR: 1.16 (s, 3H, $CH_3$), 2.05 (s, 3H, $CH_3$), 2.30 (s, 3H, $CH_3$), 2.63 (broad d, J=15.6, 2H, 2 $CH_2$), 2.88 (dd, J=15.8 and 5.8, 2H, 2 $CH_2$), 3.99 (s, 2H, $CH_2$), 6.94 (d, J=7.8, 1H, CH), 6.98 (s, 1H, CH), 7.04 (d, J=7.8, 1H, CH).

$^{13}$C-NMR: 20.89 ($CH_3$), 21.23 ($CH_3$), 24.31 ($CH_3$), 42.69 ($CH_2$), 42.99 ($CH_2$), 43.31 (C), 71.30 ($CH_2$), 124.52 (CH), 125.51 (CH), 127.13 (CH), 135.91 (C), 138.98 (C), 142.20 (C), 171.26 (CO ester).

(2,5-dimethyl-2,3-dihydro-1H-inden-2-yl)methyl propionate

¹H-NMR: 1.33 (t, J=7.6, 3H, CH₃), 1.59 (s, 3H, CH₃), 2.30 (s, 3H, CH₃), 2.33 (q, J=7.6, 2H, CH₂), 2.63 (broad d, J=15.8, 2H, CH₂), 2.88 (dd, J=15.8 and 6.0, 2H, CH₂), 4.00 (s, 2H, CH₂), 6.94 (d, J=7.6, 1 H, CH), 6.98 (s, 1H, CH), 7.04 (d, J=7.6, 1H, CH).
¹³C-NMR: 9.17 (CH₃), 21.24 (CH₃), 24.34 (CH₃), 27.61 (CH₂), 42.73 (CH₂), 43.03 (CH₂), 43.41 (C), 71.15 (CH₂), 124.51 (CH), 125.51 (CH), 127.11 (CH), 135.90 (C), 139.03 (C), 142.25 (C), 174.58 (CO ester).

(2,5-dimethyl-2,3-dihydro-1H-inden-2-yl)methyl butyrate

¹H-NMR: 0.94 (t, J=7.6, 3H, CH₃), 1.16 (s, 3H, CH₃), 1.64 (sext, J=7.6, 2H, CH₂), 2.29 (t, J=7.6, 2H, CH₂), 2.30 (s, 3H, CH₃), 2.63 (broad d, J=15.8, 2H, CH₂), 2.88 (dd, J=15.8 and 6.0, 2H, CH₂), 4.00 (s, 2H, CH₂), 6.94 (d, J=7.6, 1 H, CH), 6.98 (s, 1H, CH), 7.04 (d, J=7.6, 1H, CH).
¹³C-NMR: 13.70 (CH₃), 18.49 (CH₂), 21.23 (CH₃), 24.35 (CH₃), 36.26 (CH₂), 42.75 (CH₂), 43.05 (CH₂), 43.38 (C), 71.09 (CH₂), 124.51 (CH), 125.51 (CH), 127.11 (CH), 135.89 (C), 139.03 (C), 142.24 (C), 173.79 (CO ester).

((2,5-dimethyl-2,3-dihydro-1H-inden-2-yl)methyl isobutyrate

¹H-NMR: 1.16 (d, J=7.0, 6H, 2 CH₃), 1.16 (s, 3H, CH₃), 2.30 (s, 3H, CH₃), 2.55 (hept, J=7.0, 1 H, CH), 2.64 (broad d, J=15.8, 2H, CH₂), 2.88 (dd, J=15.8 and 6.0, 2H, CH₂), 3.99 (s, 2H, CH₂), 6.94 (d, J=7.5, 1H, CH), 6.98 (s, 1H, CH), 7.04 (d, J=7.5, 1 H, CH).
¹³C-NMR: 19.0 (2 CH₃), 21.23 (CH₃), 24.33 (CH₃), 34.13 (CH), 42.76 (CH₂), 43.06 (CH₂), 43.49 (C), 71.12 (CH₂), 124.51 (CH), 125.50 (CH), 127.11 (CH), 135.89 (C), 139.04 (C), 142.25 (C), 177.12 (CO ester).

((2,5-dimethyl-2,3-dihydro-1H-inden-2-yl)methyl pivalate

¹H-NMR: 1.17 (s, 3H, CH₃), 1.19 (s, 9H, 3 CH₃), 2.30 (s, 3H, CH₃), 2.65 (broad d, J=15.8, 2H, CH₂), 2.88 (dd, J=15.8 and 4.8, 2H, CH₂), 3.98 (s, 2H, CH₂), 6.94 (d, J=7.6, 1H, CH), 6.98 (s, 1H, CH), 7.04 (d, J=7.6, 1H, CH).
¹³C-NMR: 21.23 (CH₃), 24.34 (CH₃), 27.19 (3 CH₃), 38.92 (C), 42.80 (CH₂), 43.09 (CH₂), 43.55 (C), 71.32 (CH₂), 124.48 (CH), 125.48 (CH), 127.09 (CH), 135.86 (C), 139.04 (C), 142.26 (C), 178.48 (CO ester).

(2,5-dimethyl-2,3-dihydro-1H-inden-2-yl)methyl hexanoate

¹H-NMR: 0.83 (t, J=7.0, 3H, CH₃), 1.16 (s, 3H, CH₃), 125-1.37 (m, 4H, 2 CH₂), 1.61 (quint, J=7.5, 2H, CH₂), 2.29 (t, J=7.5, 2H, CH₁), 2.30 (s, 3H, CH₃), 2.63 (broad d, J=15.8, 2H, CH₃), 2.88 (dd, J=15.8 and 5.8, 2H, CH₂), 4.00 (s, 2H, CH₂), 6.94 (d, J=7.6, 1H, CH), 6.98 (s, 1H, CH), 7.04 (d, J=7.6, 1H, CH).
¹³C-NMR: 13.92 (CH₃), 21.23 (CH₃), 22.31 (CH₂), 24.36 (CH₃), 24.69 (CH₂), 31.34 (CH₂), 34.33 (CH₂), 42.76 (CH₂), 43.06 (CH₂), 43.38 (C), 71.12 (CH₂), 124.51 (CH), 125.50 (CH), 127.12 (CH), 135.89 (C), 139.03 (C), 142.25 (C), 173.97 (CO ester).

(2,5-dimethyl-2,3-dihydro-1H-inden-2-yl)methyl benzoate

¹H-NMR: 1.27 (s, 3H, CH₃), 2.31 (s, 3H, CH), 2.74 (broad d, J=15.8, 2H, CH₂), 3.00 (dd, J=15.8 and 3.4, 2H, CH₂), 4.24 (s, 2H, CH₂), 6.96 (d, J=7.6, 1H, CH), 7.00 (s, 1H, CH), 7.06 (d, J=7.6, 1H, CH), 7.37-7.44 (m, 2H, 2 CH), 7.53 (tt, J=7.4 and 1.3, 1 H, CH), 7.95-8.00 (m, 2H, 2 CH).
¹³C-NMR: 21.24 (CH₃), 24.47 (CH₃), 42.93 (CH₂), 43.22 (CH₂), 43.60 (C), 71.99 (CH₂), 124.51 (CH), 125.50 (CH), 127.13 (CH), 128.32 (2 CH), 129.55 (2 CH), 130.32 (C), 132.86 (CH), 135.93 (C), 139.07 (C), 142.30 (C), 166.60 (CO ester).

Example 4

Hydrogenation/Hydrogenolysis Reaction of 2,5-dimethyl-2-(((trialkylsilyl)oxy)methyl)-2,3-dihydro-1H-inden-1-one 4.1) 2,5-dimethyl-2-(((trialkylsilyl)oxy)methyl-2,3-dihydro-1H-inden-1-one Synthesis 2,5-dimethyl-2,3-dihydro-1H-inden-1-one, methanol (1 wt. eq.)) and K₂CO; (0.85 mol. %) were loaded altogether in a three-necked round-bottomed flask and heated to 60° C. Formaldehyde (1.03 mol. eq., 55 wt. % solution in water/methanol mixture) was then introduced in 1 h in order to easily control reaction exothermy. 30 minutes after addition completion (complete reaction conversion was checked by GC analysis), acetic acid (1.7 mol. %) was added to quench potassium carbonate and methanol was completely removed under reduced pressure. Obtained crude 2-(hydroxymethyl)-2,5-dimethyl-2,3-dihydro-1H-inden-1-one was then heated to 100° C. and N-(trialkylsilyl)-N-methyltrifluoroacetamide (1.4 mol. eq.) was introduced in 2 h. Reaction mixture was then heated at 140° C. for some additional 4 hours (complete reaction conversion was checked by GC analysis). After removal of lights (excess silylating agent and N-methyltrifluoracetamide formed) 2,5-dimethyl-2-(((trialkylsilyl)oxy)methyl)-2,3-dihydro-1H-inden-1-one were purified by distillation under vacuum.

2,5-dimethyl-2-(((trimethylsilyl)oxy)methyl)-2,3-dihydro-1H-inden-1-one was thus obtained as a colorless viscous liquid with 90% yield in 98% GC purity.

¹H-NMR: 0.01 (s, 9H, 3 CH₃), 1.13 (s, 3H, CH₃), 2.42 (s, 3H, CH₃), 2.74 (d, J=17.0, 1H, CH₂), 3.34 (d, J=17.0, 1H, CH₂), 3.50 (d, J=9.7, 1H, CH₂), 3.76 (d, J=9.7, 1H, CH₂), 7.14 (d, J=7.6, 1H, CH), 7.23 (s, 1H, CH), 7.61 (d, J=7.6, 1H, CH).
¹³C-NMR: –0.62 (3 CH₃), 20.55 (CH₃), 22.08 (CH₃), 37.68 (CH₂), 51.57 (C), 67.49 (CH₂), 123.82 (CH), 126.86 (CH), 128.40 (CH), 134.10 (C), 145.80 (C), 154.01 (C), 209.40 (CO ketone).

2,5-dimethyl-2-(((tert-butyldimethylsilyl)oxy)methyl)-2,3-dihydro-1H-inden-1-one was thus obtained as a slightly yellow viscous liquid with 40% yield in 98% GC purity.

¹H-NMR: –0.08 (s, 3H, CH), –0.02 (s, 3H, CH₃), 0.71 (s, 9H, 3 CH), 1.14 (s, 3H, CH₃), 2.42 (s, 3H, CH₃), 2.76 (d, J=17.0, 1H, CH₂), 3.34 (d, J=17.0, 1H, CH₂), 3.52 (d, J=9.4, 1H, CH₂), 3.78 (d, J=9.4, 1H, CH₂), 7.14 (d, J=7.8, 1H, CH), 7.23 (s, 1H, CH), 7.61 (d, J=7.8, 1 H, CH).

$^{13}$C-NMR: −5.64 (CH$_3$), −5.62 (CH$_3$), 17.99 (C), 20.21 (CH$_3$), 22.07 (CH$_2$), 25.59 (3 CH$_3$), 37.90 (CH$_2$), 51.65 (C), 68.28 (CH$_2$), 123.70 (CH), 126.71 (CH), 128.32 (CH), 134.36 (C), 145.72 (C), 154.13 (C), 209.55 (CO ketone).

4.2) 2,5-dimethyl-2-(((trialkylsilyl)oxy)methyl)-2,3-dihydro-1H-inden-1-one Hydrogenation/Hydrogenolysis Reaction Neat distilled 2,5-dimethyl-2-(((trialkylsilyl)oxy) methyl)-2,3-dihydro-1H-inden-1-one, acetic acid (2 mol. eq.), carboxylic anhydride (0.6 mol. eq.) and Pd/C (0.30 mol. % Pd) were loaded altogether in an autoclave. After purging with nitrogen (3 times 5 bars) and hydrogen (3 times 5 bars), the autoclave was pressurized to 30 bars hydrogen and progressively heated to 140° C. while maintaining hydrogen pressure constant during the whole reaction. After complete conversion (checked by GC analysis) or 24 h in case of partial conversion, the autoclave was cooled down to room temperature, depressurized and purged with nitrogen. Heterogeneous catalyst was then filtered off and remaining organic phase was concentrated under vacuum for lights removal. Desired product was generally obtained as a mixture of free alcohol (minor), acetate (major) and initial silyl ether derivative (minor). Reaction yields were determined after bulb to bulb distillation in order to determine the quantity of residues eventually formed during de reaction and quantitative saponification and final deprotection reaction using tetrabutylammonium fluoride in THF to afford (2,5-dimethyl-2,3-dihydro-1H-inden-2-yl)methanol as the sole product.

| Silyl ether substrate | Time to completion (h) | Selectivity (GC %) | Alcohol/acetate/ether GC % ratio [a] | Yield [b] (mol. %) |
|---|---|---|---|---|
| OSi(CH$_3$)$_3$ | 24 h | 95% | 1/98/1 | 94% |
| OSi(CH$_3$)$_2$(C(CH$_3$)$_3$) | 24 h | 97% | 1/52/47 | 96% |

[a] alcohol/acetate/ether ratio is depending on reaction duration
[b] final yield in (2,5-dimethyl-2,3-dihydro-1H-inden-2-yl)methanol
c) ((2,5-dimethyl-2,3-dihydro-1H-inden-2-yl)methyl acetate and tert-butyl((2,5-dimethyl-2,3-dihydro-1H-inden-2-yl)methoxy)dimethylsilane were unexpectedly obtained as acetate and silyl ether reaction products.

((2,5-dimethyl-2,3-dihydro-1H-inden-2-yl)methoxy) trimethylsilane $^1$H-NMR: 0.08 (s, 9H, 3 CH$_3$), 1.03 (s, 3H, CH$_3$), 2.22 (s, 3H, CH$_3$), 2.44 (dd, J=15.8 and 3.4, 2H, CH$_2$), 2.78 (dd, =15.8 and 5.4, 2H, CH$_2$), 3.32 (s, 2H, CH$_2$), 6.84 (d, J=7.6, 1H, CH), 6.89 (s, 1H, CH), 6.95 (d, J=7.6, 1H, CH).
$^{13}$C-NMR: −0.50 (3 CH$_3$), 21.25 (CH$_3$), 24.24 (CH$_3$), 42.22 (CH$_2$), 42.56 (CH$_2$), 45.17 (C), 69.58 (CH$_2$), 124.51 (CH), 125.52 (CH), 126.80 (CH), 135.53 (C), 139.86 (C), 143.10 (C).

tert-butyl((2,5-dimethyl-2,3-dihydro-1H-inden-2-yl) methoxy)dimethylsilane $^1$H-NMR: 0.02 (s, 6H, 2 CH$_3$), 0.88 (s, 9H, 3 CH$_3$), 1.11 (s, 3H, CH$_3$), 2.30 (s, 3H, CH$_3$), 2.53 (dd, J=16.0 and 2.5, 2H, CH$_2$), 2.86 (dd, J=16.0 and 5.2, 2H, CH$_2$), 3.42 (s, 2H, CH$_2$), 6.92 (d, J=7.6, 1 H, CH), 6.97 (s, 1H, CH), 7.03 (d, J=7.6, 1H, CH).
$^{13}$C-NMR: −5.44 (2 CH$_3$), 18.30 (C), 21.25 (CH$_3$), 24.28 (CH$_3$), 25.90 (3 CH$_3$), 42.27 (CH$_2$), 42.59 (CH$_2$), 45.38 (C), 70.15 (CH$_2$), 124.49 (CH), 125.51 (CH), 126.77 (CH), 135.49 (C), 139.93 (C), 143.17 (C).

Example 5

Derivatives from Aromatic Ring Substitution

Starting from previously described substituted 2-methyl-2,3-dihydro-1H-inden-1-one, the corresponding (2-methyl-1-oxo-2,3-dihydro-1H-inden-2-yl)methyl acetate, (2-methyl-2,3-dihydro-1H-inden-2-yl)methyl acetate and (2-methyl-2,3-dihydro-1H-inden-2-yl)methanol derivatives were obtained according to the same procedures as the ones described in 3.1 and 3.2.

5.1) From 2-methyl-2,3-dihydro-1H-inden-1-one

Starting from 2-methyl-2,3-dihydro-1H-inden-1-one, (2-methyl-1-oxo-2,3-dihydro-1H-inden-2-yl)methyl acetate was obtained as a colorless liquid with 95% molar yield in 98% GC purity.
$^1$H-NMR: 1.24 (s, 3H, CH$_3$), 1.92 (s, 3H, CH$_3$), 2.92 (d, J=17.2, 1H, CH$_2$), 3.27 (d, J=17.2, 1H, CH$_2$), 4.20 (d, J=10.8, 1H, CH$_2$), 4.24 (d, J=10.8, 1H, CH$_2$), 7.39 (td, J=7.4 and 0.8, 1 H, CH), 7.47 (dt, J=7.8 and 0.8, 1H, CH), 7.62 (td, J=7.4 and 1.2, 1H, CH), 7.77 (d, J=7.8, 1H, CH).
$^{13}$C-NMR: 20.68 (CH$_3$), 21.09 (CH$_3$), 38.04 (CH$_2$), 48.87 (C), 68.26 (CH$_2$), 124.40 (CH), 126.61 (CH), 127.58 (CH), 135.15 (CH), 135.60 (C), 152.47 (C), 170.83 (CO ester), 207.97 (CO ketone).

Starting from (2-methyl-1-oxo-2,3-dihydro-1H-inden-2-yl)methyl acetate, (2-methyl-2,3-dihydro-1H-inden-2-yl) methyl acetate was obtained as a colorless liquid with 98% molar yield in 98% GC purity.
$^1$H-NMR: 1.17 (s, 3H, CH$_3$), 2.04 (s, 3H, CH$_3$), 2.68 (d, J=15.6, 2H, 2 CH$_2$), 2.93 (d, J=15.6, 2H, 2 CH$_2$), 4.00 (s, 2H, CH$_2$), 7.10-7.18 (m, 41-1, 4 CH).
$^{13}$C-NMR: 20.88 (CH$_3$), 24.27 (CH$_3$), 43.09 (2 CH$_2$), 43.18 (C), 71.26 (CH$_2$), 124.80 (2 CH), 126.35 (2 CH), 142.07 (2C), 171.27 (CO ester).

Starting from (2-methyl-2,3-dihydro-1H-inden-2-yl) methyl acetate, (2-methyl-2,3-dihydro-1H-inden-2-yl) methanol was obtained as a colorless liquid in quantitative molar yield.
$^1$H-NMR: 1.17 (s, 3H, CH$_3$), 1.76 (broad s, 1H, OH), 2.64 (d, J=15.8, 2H, 2 CH$_2$), 2.90 (d, J=15.8, 2H, 2 CH$_2$), 3.50 (s, 2H, CH$_2$), 7.09-7.19 (m, 4H, 4 CH).
$^{13}$C-NMR: 23.98 (CH$_3$), 42.74 (2 CH$_2$), 44.92 (C), 70.54 (CH$_2$), 124.82 (2 CH), 126.21 (2 CH), 142.50 (2C).

5.2) From 5-isopropyl-2-methyl-2,3-dihydro-1H-inden-1-one

Starting from 5-isopropyl-2-methyl-2,3-dihydro-1H-inden-1-one, (5-isopropyl-2-methyl-1-oxo-2,3-dihydro-1H-inden-2-yl)methyl acetate was obtained as a colorless viscous liquid with 96% yield in 98% GC purity.
$^1$H-NMR: 1.23 (s, 3H, CH$_3$), 1.30 (d, J=6.9, 6H, 2 CH$_3$), 1.93 (s, 3H, CH$_3$), 2.88 (d, J=17.0, 1H, CH$_2$), 3.00 (hept, J=6.9, 1H, CH), 3.23 (d, J=17.0, 1H, CH$_2$), 4.19 (d, J=10.8, 1H, CH$_2$), 4.22 (d, J=10.8, 1H, CH$_2$), 7.26 (d, J=7.9, 1H, CH), 7.30 (s, 1H, CH), 7.69 (d, J=7.9, 1H, CH).

$^{13}$C-NMR: 20.73 (CH$_3$), 21.18 (CH$_3$), 23.75 (2 CH$_3$), 34.72 (CH), 38.00 (CH$_2$), 49.07 (C), 68.29 (CH$_2$), 124.22 (CH), 124.39 (CH), 126.51 (CH), 133.66 (C), 152.99 (C), 157.20 (C), 170.89 (CO ester), 207.43 (CO ketone).

Starting from (5-isopropyl-2-methyl-1-oxo-2,3-dihydro-1H-inden-2-yl)methyl acetate, (5-isopropyl-2-methyl-2,3-dihydro-1H-inden-2-yl)methyl acetate was obtained as a colorless viscous liquid with 96% yield in 98.5% GC purity.

$^1$H-NMR: 1.17 (s, 3H, CH$_3$), 1.23 (d, J=6.9, 6H, 2 CH$_3$), 2.04 (s, 3H, CH$_3$), 2.65 (dd, J=15.8 and 6.6, 2H, CH$_2$), 2.86 (hept, J=6.9, 1H, CH), 2.90 (dd, J=15.8 and 8.0, 2H, CH$_2$), 3.99 (s, 2H, CH$_2$), 6.99 (d, J=7.8, 1H, CH), 7.03 (s, 1H, CH), 7.07 (d, J=7.8, 1H, CH).

$^{13}$C-NMR: 20.89 (CH$_3$), 24.24 (2 CH$_3$), 24.38 (CH$_3$), 33.98 (CH), 42.73 (CH$_2$), 43.0) (CH$_2$), 43.28 (C), 71.34 (CH$_2$), 122.77 (CH), 124.55 (CH), 124.61 (CH), 139.43 (C), 142.16 (C), 147.25 (C), 171.29 (CO ester).

Starting from (5-isopropyl-2-methyl-2,3-dihydro-1H-inden-2-yl)methyl acetate, (5-isopropyl-2-methyl-2,3-dihydro-1H-inden-2-yl)methanol was obtained as a colorless viscous liquid in quantitative molar yield.

$^1$H-NMR: 1.17 (s, 3H, CH$_3$), 1.23 (d, J=6.9, 6H, 2 CH$_3$), 1.75 (broad t, J=5.4, 1H, OH), 2.62 (dd, J=15.8 and 7.5, 2H, CH$_2$), 2.81-2.92 (m, 3H, CH+CH$_2$), 3.50 (d, J=5.4, 2H, CH$_2$), 6.99 (d, J=7.6, 1H, CH), 7.03 (s, 1H, CH), 7.07 (d, J=7.6, 1H, CH).

$^{13}$C-NMR: 24.11 (CH$_3$), 24.25 (2CH$_3$), 33.96 (CH), 42.42 (CH$_2$), 42.77 (CH$_2$), 45.00 (C), 70.69 (CH$_2$), 122.80 (CH), 124.49 (CH), 124.55 (CH), 139.83 (C), 142.57 (C), 147.12 (C).

5.3) From 2,4-dimethyl-2,3-dihydro-1H-inden-1-one

Starting from 2,4-dimethyl-2,3-dihydro-1H-inden-1-one, (2,4-dimethyl-1-oxo-2,3-dihydro-1H-inden-2-yl)methyl acetate was obtained as a colorless viscous liquid with 95% yield in 97.5% GC purity.

$^1$H-NMR: 1.24 (s, 3H, CH$_3$), 1.93 (s, 3H, CH$_3$), 2.36 (s, 3H, CH$_2$), 2.81 (d, J=17.2, 1H, CH$_2$), 3.14 (d, J=17.2, 1H, CH$_2$), 4.21 (d, J=11.2, 2H, CH$_2$), 4.24 (d, J=11.2, 2H, CH$_2$), 7.31 (t, J=7.6, 1H, CH), 7.44 (d, J=7.6, 1H, CH), 7.61 (t, J=7.6, 1H, CH).

$^{13}$C-NMR: 17.81 (CH$_3$), 20.69 (CH$_3$), 21.24 (CH$_3$), 37.02 (CH$_2$), 48.84 (C), 68.35 (CH$_2$), 121.77 (CH), 127.80 (CH), 135.39 (C), 135.60 (CH), 135.79 (C), 151.41 (C), 170.82 (CO ester), 208.2 (CO ketone).

Starting from (2,4-dimethyl-1-oxo-2,3-dihydro-1H-inden-2-yl)methyl acetate, (2,4-dimethyl-2,3-dihydro-1H-inden-2-yl)methyl acetate was obtained as a colorless viscous liquid with 95% yield in 97.5% GC purity.

$^1$H-NMR: 1.17 (s, 3H, CH$_3$), 2.05 (s, 3H, CH$_3$), 2.22 (s, 3H, CH$_3$), 2.61 (d, J=16.0, 1H, CH$_2$), 2.61 (d, J=16.0, 1H, CH$_2$), 2.84 (d, J=16.0, 1H, CH$_2$), 2.94 (d, J=16.0, 1H, CH$_2$), 4.00 (d, J=1.0, 2H, CH$_2$), 6.93 (d, J=7.6, 1 H, CH), 6.99 (d, J=7.6, 1H, CH), 7.04 (t, J=7.6, 1 H, CH).

$^{13}$C-NMR: 19.03 (CH$_3$), 20.86 (CH$_3$), 24.62 (CH$_3$), 41.85 (CH$_2$), 42.58 (C), 43.34 (CH$_2$), 71.45 (CH$_2$), 122.10 (CH), 126.59 (CH), 127.20 (CH), 134.12 (C), 140.87 (C), 141.77 (C), 171.27 (CO ester).

Starting from (2,4-dimethyl-2,3-dihydro-1H-inden-2-yl)methyl acetate, (2,4-dimethyl-2,3-dihydro-1H-inden-2-yl)methanol was obtained as a colorless viscous liquid in quantitative molar yield.

$^1$H-NMR: 1.17 (s, 3H, CH$_3$), 1.83 (broad t, J=5.6, 1H, OH), 2.21 (s, 3H, CH$_3$), 2.57 (d, J=16.0, 1 H, CH$_2$), 2.66 (d, J=16.0, 1 H, CH$_2$), 2.83 (d, J=16.0, 1H, CH$_2$), 2.91 (d, J=16.0, 1 H, CH$_2$), 3.50 (d, J=5.6, 2H, CH$_2$), 6.93 (d, J=7.2, 1H, CH), 6.98 (d, J=7.2, 1H, CH), 7.04 (t, J=7.2, 1H, CH).

$^{13}$C-NMR: 19.04 (CH$_3$), 24.34 (CH$_3$), 41.50 (CH$_2$), 43.04 (CH$_2$), 44.25 (C), 70.77 (CH$_2$), 122.11 (CH), 126.46 (CH), 127.05 (CH), 134.13 (C), 141.31 (C), 142.18 (C).

5.4) From 2,6-dimethyl-2,3-dihydro-1H-inden-1-one

Starting from 2,6-dimethyl-2,3-dihydro-1H-inden-1-one, (2,6-dimethyl-1-oxo-2,3-dihydro-1H-inden-2-yl)methyl acetate was obtained as a colorless viscous liquid with 96% yield in 98.0% GC purity.

$^1$H-NMR: 1.22 (s, 3H, CH), 1.91 (s, 3H, CH$_3$), 2.41 (s, 3H, CH$_3$), 2.87 (d, J=17.0, 1H, CH$_2$), 3.22 (d, J=17.0, 1H, CH$_2$), 4.19 (d, J=11.0, 1H, CH$_2$), 4.22 (d, J=11.0, 1H, CH$_2$), 7.35 (d, J=7.8, 1H, CH), 7.44 (d, J=7.8, 1H, CH), 7.56 (s, 1H, CH).

$^{13}$C-NMR: 20.67 (CH$_3$), 21.07 (CH$_3$), 21.14 (CH$_2$), 37.71 (CH$_2$), 49.19 (C), 68.31 (CH$_2$), 124.28 (CH), 126.30 (CH), 135.76 (C), 136.43 (CH), 137.51 (C), 149.81 (C), 170.81 (CO ester), 207.99 (CO ketone).

Starting from (2,6-dimethyl-1-oxo-2,3-dihydro-1H-inden-2-yl)methyl acetate, (2,5-dimethyl-2,3-dihydro-1H-inden-2-yl)methyl acetate was obtained as a colorless viscous liquid with 96% yield in 98.0% GC purity.

(See above for NMR data)

Starting from ((2,5-dimethyl-2,3-dihydro-1H-inden-2-yl)methyl acetate, (2,5-dimethyl-2,3-dihydro-1H-inden-2-yl)methanol was obtained as a colorless viscous liquid with quantitative molar yield.

(See above for NMR data)

5.5) From 2,4,5-trimethyl-2,3-dihydro-1H-inden-1-one

Starting from 2,4,5-trimethyl-2,3-dihydro-1H-inden-1-one, (2,4,5-trimethyl-1-oxo-2,3-dihydro-1H-inden-2-yl)methyl acetate was obtained as a colorless viscous liquid with 95% yield in 98.0% GC purity.

$^1$H-NMR: 1.23 (s, 3H, CH$_3$), 1.93 (s, 3H, CH$_3$), 2.25 (s, 3H, CH$_3$), 2.38 (s, 3H, CH$_3$), 2.82 (d, J=17.1, 1H, CH$_2$), 3.14 (d, J=17.1, 1H, CH$_2$), 4.20 (d, J=10.6, 1H, CH$_2$), 4.23 (d, J=10.6, 1H, CH$_2$), 7.20 (d, J=7.8, 1H, CH), 7.53 (d, J=7.8, 1H, CH).

$^{13}$C-NMR: 14.57 (CH$_3$), 20.34 (CH$_3$), 20.73 (CH$_3$), 21.36 (CH$_3$), 37.37 (CH$_2$), 49.09 (C), 68.39 (CH$_2$), 121.58 (CH), 129.83 (CH), 133.47 (C), 133.97 (C), 144.43 (C), 151.55 (C), 170.87 (CO ester), 207.89 (CO ketone).

Starting from (2,4,5-trimethyl-1-oxo-2,3-dihydro-1H-inden-2-yl)methyl acetate, (2,4,5-trimethyl-2,3-dihydro-1H-inden-2-yl)methyl acetate was obtained as a colorless viscous liquid with 97% yield in 98.0% GC purity.

$^1$H-NMR: 1.17 (s, 3H, CH$_3$), 2.05 (s, 3H, CH$_3$), 2.13 (s, 3H, CH$_3$), 2.23 (s, 3H, CH$_3$), 2.62 (d, J=16.0, 114, CH$_2$), 2.65 (d, J=16.0, 1H, CH$_2$), 2.86 (d, J=16.0, 1H, CH$_2$), 2.92 (d, J=16.0, 1H, CH$_2$), 3.99 (d, J=10.8, 1H, CH$_2$), 4.02 (d, J=10.8, 1H, CH$_2$), 6.89 (d, J=7.6, 1 H, CH), 6.94 (d, J=7.6, 1H, CH).

$^{13}$C-NMR: 15.77 (CH$_3$), 19.57 (CH$_3$), 20.88 (CH$_3$), 24.68 (CH$_3$), 42.31 (CH$_2$), 42.74 (C), 43.24 (CH$_2$), 71.49 (CH$_2$), 121.77 (CH), 128.14 (CH), 132.60 (C), 134.23 (C), 139.26 (C), 141.04 (C), 17125 (CO ester).

Starting from (2,4,5-trimethyl-2,3-dihydro-1H-inden-2-yl)methyl acetate, (2,4,5-trimethyl-2,3-dihydro-1H-inden-2-yl)methanol was obtained as a colorless viscous liquid in quantitative molar yield.

$^1$H-NMR: 1.17 (s, 3H, CH$_3$), 1.83 (broad s, 1H, OH), 2.13 (s, 3H, CH$_3$), 2.23 (s, 3H, CH$_3$), 2.59 (d, J=16.0, 1H, CH$_2$), 2.63 (d, J=16.0, 1H, CH$_2$), 2.85 (d, J=16.0, 1H, CH$_2$), 2.87 (d, J=16.0, 1H, CH$_2$), 3.49 (broad s, 2H, CH$_2$), 6.89 (d, J=7.8, 1H, CH), 6.94 (d, J=7.8, 1H, CH).

$^{13}$C-NMR: 15.76 (CH$_3$), 19.57 (CH$_4$), 24.39 (CH$_3$), 42.00 (CH$_2$), 42.96 (CH$_2$), 44.42 (C), 70.87 (CH$_2$), 121.76 (CH), 128.02 (CH), 132.59 (C), 134.08 (C), 139.68 (C), 141.48 (C).

5.6) From
2,5,6-trimethyl-2,3-dihydro-1H-inden-1-one

Starting from 2,5,6-trimethyl-2,3-dihydro-1H-inden-1-one, (2,5,6-trimethyl-1-oxo-2,3-dihydro-1H-inden-2-yl)methyl acetate was obtained as a colorless viscous liquid with 95% yield in 98.0% GC purity.

$^1$H-NMR: 1.21 (s, 3H, CH$_3$), 1.92 (s, 3H, CH$_3$), 2.31 (s, 3H, CH$_3$), 2.35 (s, 3H, CH$_3$), 2.83 (d, J=17.0, 1H, CH$_2$), 3.18 (d, J=17.0, 1H, CH$_2$), 4.18 (d, J=10.8, 1H, CH$_2$), 4.21 (d, J=10.8, 1H, CH$_2$), 7.23 (s, 1H, CH), 7.53 (s, 1H, CH).

$^{13}$C-NMR: 19.72 (CH$_3$), 20.70 (CH$_3$), 20.76 (CH$_3$), 21.22 (CH), 37.61 (CH$_2$), 49.02 (C), 68.34 (CH$_2$), 124.69 (CH), 127.35 (CH), 133.73 (C), 136.52 (C), 145.62 (C), 150.59 (C), 170.85 (CO ester), 207.60 (CO ketone).

Starting from (2,5,6-trimethyl-1-oxo-2,3-dihydro-1H-inden-2-yl)methyl acetate, (2,5,6-trimethyl-2,3-dihydro-1H-inden-2-yl)methyl acetate was obtained as a colorless viscous liquid with 98% yield in 98.0% GC purity.

$^1$H-NMR: 1.15 (s, 3H, CH$_3$), 2.04 (s, 3H, CH$_3$), 2.21 (s, 6H, 2 CH$_3$), 2.60 (d, J=15.6, 2H, 2 CH$_2$), 2.86 (d, J=15.6, 2H, 2 CH$_2$), 3.99 (s, 2H, CH$_2$), 6.94 (s, 2H, 2 CH).

$^{13}$C-NMR: 19.69 (2 CH$_3$), 20.86 (CH$_3$), 24.38 (CH$_3$), 42.80 (2 CH$_2$), 43.29 (C), 71.36 (CH$_2$), 125.97 (2 CH), 134.47 (2C), 139.54 (2C), 171.23 (CO ester).

Starting from (2,5,6-trimethyl-2,3-dihydro-1H-inden-2-yl)methyl acetate, (2,5,6-trimethyl-2,3-dihydro-1H-inden-2-yl)methanol was obtained as a colorless viscous liquid in quantitative molar yield.

$^1$H-NMR: 1.15 (s, 3H, CH$_3$), 1.80 (broad s, 1H, OH), 2.21 (s, 6H, 2 CH$_3$), 2.58 (d, J=15.8, 2H, 2 CH), 2.83 (d, J=15.8, 2H, 2 CH$_2$), 3.48 (broad s, 2H, CH$_2$), 6.94 (s, 2H, 2 CH).

$^{13}$C-NMR: 19.69 (2 CH$_3$), 24.09 (CH$_3$), 42.48 (2 CH$_2$), 45.00 (C), 70.74 (CH$_2$), 125.97 (2 CH), 134.32 (2C), 139.97 (C).

What is claimed is:

1. A process for the preparation of a compound of formula

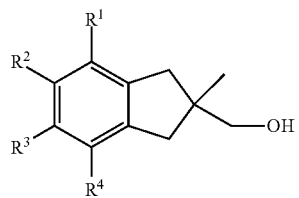

(I)

in the form of any one of its stereoisomers or a mixture thereof, and wherein each R$^1$, R$^2$, R$^3$ and R$^4$, independently from each other, represents a hydrogen atom or a C$_{1-3}$ alkyl group;

characterized in that said process comprises the steps of:
a) reducing a precursor compound of the formula

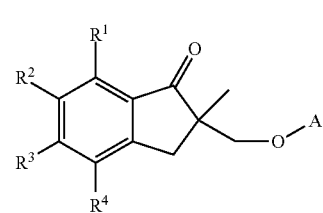

(II)

in the form of any one of its stereoisomers or a mixture thereof, and wherein each R$^1$, R$^2$, R$^3$ and R$^4$, is defined as in formula (I); and A represents a C$_{3-10}$ trialkylsilyl or an RCO group wherein R represents a hydrogen atom, a C$_{1-8}$ alkyl group, or a phenyl optionally substituted by one to three groups selected amongst a C$_{1-3}$ alkyl, alkoxy or amine group;

into an indane of formula

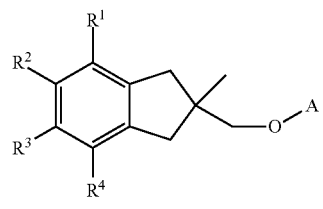

(III)

in the form of any one of its stereoisomers or a mixture thereof, and wherein each R$^1$, R$^2$, R$^3$, R$^4$ and A is defined as in formula (II); and b) hydrolysing the indane of formula (III) into the compound of formula (I).

2. A process according to claim 1, characterised in that compound of formula (II) is of formula

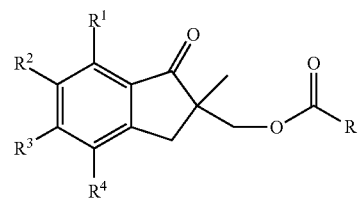

(II')

wherein each R$^1$, R$^2$, R$^3$, R$^4$ and R are as defined in claim 1;
and said compound of formula (III) is of formula

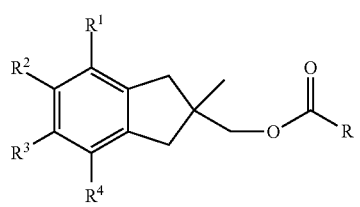

(III')

wherein each $R^1$, $R^2$, $R^3$, $R^4$ and R are as defined in claim 1.

3. The process of claim 1, wherein at least one of said $R^1$, $R^2$, $R^3$ and $R^4$ is a $C_{1-3}$ alkyl group.

4. The process of claim 1, wherein the R group represents a $C_{1-4}$ alkyl group.

5. The process of claim 1, wherein the reduction of step a) is performed by a catalytic hydrogenation in the presence of a supported Pd.

6. A process according to claim 5, characterised in that said supported Pd is a Pd on charcoal having an egg-shell-type distribution.

7. A compound of formula

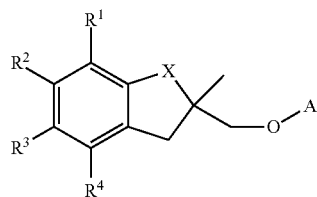

(IV)

in the form of any one of its stereoisomers or a mixture thereof, and wherein X represents a $CH_2$ or C=O group; each $R^1$, $R^2$, $R^3$, and $R^4$ independently from each other, represents a hydrogen atom or a $C_{1-3}$ alkyl group; and A represents a $C_{3-10}$ trialkylsilyl or an RCO group wherein R represents a hydrogen atom, a $C_{1-8}$ alkyl group, or a phenyl optionally substituted by one to three groups selected amongst a $C_{1-3}$ alkyl, alkoxy or amine group, provided that (2-methyl-1-oxo-2,3-dihydro-1H-inden-2-yl)methyl acetate, (2-methyl-1-oxo-2,3-dihydro-1H-inden-2-yl)methyl formate, (2-methyl-1-oxo-2,3-dihydro-1H-inden-2-yl)methyl benzoate, ((2-methyl-2,3-dihydro-1H-inden-2-yl)methyl acetate, (6-methyl-2-methyl-1-oxo-2,3-dihydro-1H-inden-2-yl)methyl acetate and (5-ethyl-2-methyl-2,3-dihydro-1H-inden-2-yl)methyl acetate are excluded.

8. The compound of claim 7, wherein said compound is of formula

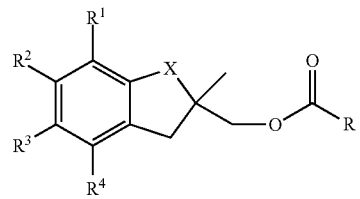

(IV)

in the form of any one of its stereoisomers or a mixture thereof, and wherein X represents a $CH_2$ or C=O group; and each $R^1$, $R^2$, $R^3$, and $R^4$, independently from each other, represents a hydrogen atom or a $C_{1-3}$ alkyl group, and R represents a hydrogen atom, a $C_{1-8}$ alkyl group, or a phenyl optionally substituted by one to three groups selected amongst a $C_{1-3}$ alkyl, alkoxy or amine group.

9. A compound according to claim 8, characterised in that X is a carbonyl group.

10. A compound according to claim 8, characterised in that X is a $CH_2$ group.

11. The compound of claim 8, wherein:
i) $R^1$, $R^2$ and $R^4$ are each a hydrogen atom and $R^3$ is a methyl group, ii) $R^1$, $R^2$ and $R^3$ are each a hydrogen atom and $R^4$ is a methyl group, iii) $R^1$ and $R^4$ are each a hydrogen atom and $R^2$ and $R^3$ are each a methyl group, iv) $R^1$ and $R^3$ are each a hydrogen atom and $R^2$ and $R^4$ are each a methyl group or v) $R^1$ and $R^2$ are each a hydrogen atom and $R^3$ and $R^4$ are each a methyl group.

12. The process of claim 2, wherein at least one of the $R^1$, $R^2$, $R^3$ and $R^4$ is a $C_{1-3}$ alkyl group.

13. The process of claim 2, wherein the R group represents a $C_{1-4}$ alkyl group.

14. The process of claim 2, wherein the reduction of step a) is performed by a catalytic hydrogenation in the presence of a supported Pd.

15. The process of claim 14, wherein the supported Pd is a Pd on charcoal having an egg-shell-type distribution.

* * * * *